US 6,526,804 B2

United States Patent
Takahashi (10) Patent No.: US 6,526,804 B2
(45) Date of Patent: Mar. 4, 2003

(54) ROAD FRICTION COEFFICIENT ESTIMATING APPARATUS FOR VEHICLE

(75) Inventor: Akira Takahashi, Tokyo (JP)

(73) Assignee: Fuji Jukogyo KabushikI Kaisha, Tokyo (JP)

( * ) Notice: Subject to any disclaimer, the term of this patent is extended or adjusted under 35 U.S.C. 154(b) by 0 days.

(21) Appl. No.: 09/866,769

(22) Filed: May 30, 2001

(65) Prior Publication Data
US 2002/0007661 A1 Jan. 24, 2002

(30) Foreign Application Priority Data
May 30, 2000 (JP) ....................................... 2000-160939

(51) Int. Cl.⁷ ............................................. G01N 19/02
(52) U.S. Cl. .................................. 73/9; 702/85; 701/80
(58) Field of Search .............................. 73/9, 8; 701/80, 701/82; 303/150

(56) References Cited

U.S. PATENT DOCUMENTS

| | | | | |
|---|---|---|---|---|
| 4,984,163 A | * | 1/1991 | Kuwana et al. | 364/426.02 |
| 5,466,054 A | * | 11/1995 | Okazaki | 303/150 |
| 5,480,221 A | * | 1/1996 | Morita et al. | 303/113.5 |
| 5,668,724 A | * | 9/1997 | Ehret et al. | 701/80 |
| 5,723,768 A | * | 3/1998 | Ammon | 73/8 |
| 5,765,119 A | * | 6/1998 | Otabe et al. | 701/82 |
| 5,814,718 A | * | 9/1998 | Andresen et al. | 73/9 |
| 5,863,105 A | * | 1/1999 | Sano | 303/146 |
| 5,878,365 A | * | 3/1999 | Onogi et al. | 701/70 |
| 5,944,392 A | * | 8/1999 | Tachihata et al. | 303/112 |
| 5,948,961 A | * | 9/1999 | Asano et al. | 73/9 |
| 6,023,649 A | * | 2/2000 | Matsuura et al. | 701/71 |
| 6,062,659 A | * | 5/2000 | Matsuda | 303/160 |
| 6,163,747 A | * | 12/2000 | Matsuno | 701/80 |
| 6,254,204 B1 | * | 7/2001 | Hara et al. | 303/183 |
| 6,302,500 B1 | * | 10/2001 | Aizawa | 303/173 |
| 6,324,461 B1 | * | 11/2001 | Yamaguchi et al. | 701/80 |
| 2002/0007661 A1 | * | 1/2002 | Takahashi | 73/9 |

FOREIGN PATENT DOCUMENTS

| | | | |
|---|---|---|---|
| JP | 10-242030 | | 9/1998 |
| JP | 11-101732 | * | 4/1999 ......... G01N/19/02 |
| JP | 11-267730 | | 10/1999 |

* cited by examiner

Primary Examiner—Hezron Williams
Assistant Examiner—Charles D. Garber
(74) Attorney, Agent, or Firm—Smith, Gambrell & Russell, LLP (57) ABSTRACT

A yaw rate comparison road friction coefficient estimating section estimates a first road friction coefficient based on a high friction road reference yaw rate calculated according to a high friction coefficient road vehicle motion model in a high friction road reference value estimating section, a low friction road reference yaw rate calculated according to a low friction coefficient road vehicle motion model in a low friction road reference value estimating section, and an actual yaw rate calculated in an actual value estimating section. A final road friction coefficient estimating section calculates a present final road friction coefficient by weight-averaging a previous final road friction coefficient and the first road friction coefficient using a weight function established in a weight function establishing section. The weight function is variable according to a road roughness parameter produced in a road roughness detecting apparatus.

9 Claims, 4 Drawing Sheets

ROAD FRICTION COEFFICIENT ESTIMATING APPARATUS FOR VEHICLE

BACKGROUND OF THE INVENTION

1. Field of the Invention

The present invention relates to an apparatus for estimating friction coefficient between tire and road surface and more particularly an apparatus for properly estimating friction coefficient between tire and road surface according to vehicle traveling conditions.

2. Discussion of Related Arts

In recent years, numerous vehicle control technologies such as a traction control technology, a braking force control technology, a torque distribution control technology and the like, have been proposed and some of these control technologies have been realized in actual automobile markets. Many of these control technologies use a friction coefficient between tire and road surface (hereinafter, referred to as road friction coefficient) for calculation or correction of control parameters. Accordingly, in order to make the control sure and precise, it is necessary to estimate accurate road friction coefficients. Several technologies in which road friction coefficients are estimated by comparing actual values (values detected by sensors, values estimated by observers) with reference values of parameters obtained from a vehicle motion model, have been proposed. For example, in Japanese Patent Application Unexamined No. Toku-Gan-Hei 10-242030, the applicant of the present invention proposes technologies wherein road friction coefficients are estimated by comparing slip angles estimated by observers with reference values of slip angles based on a vehicle motion model on road surface with high friction coefficients or on road surface with low friction coefficients.

In case where physical quantities such as road friction coefficients which are unable to be measured directly are estimated, generally their responsiveness, accuracy and stability are in a trade-off relationship with each other. That is, if the control system tries to catch changes of road friction coefficients quickly, there is a high possibility that the control system responds to disturbances and sensor noises and as a result road friction coefficients are erroneously estimated. On the other hand, in order to avoid this erroneous estimation, the deviation of road friction coefficients must be deleted by processes such as applying a strong filtering process in the calculation of road friction coefficients.

Specifically, in case where a vehicle enters from a dry paved road into a frozen road during traveling, road friction coefficients abruptly change from a high friction state to a low friction state. In this situation, it is necessary to recognize that the vehicle comes into a road surface having low friction coefficients as soon as possible. However, in case of a small steering angle, or in case of detecting a small yaw rate value or in case of detecting a small lateral acceleration value, sometimes the recognition of low road friction coefficients is delayed. On the other hand, in case where this recognition of low road friction coefficients is too sensitive, small noises make the road friction coefficient estimating apparatus erroneously recognize normal dry roads as roads having low friction coefficients.

To solve this problem, in Japanese Patent Application Laid-open Toku-Gan-Hei 11-267730, the road friction coefficient estimating apparatus includes a road friction coefficient estimating means dedicated to a road surface with low friction coefficient in the road friction coefficient estimating means so as to swiftly be able to establish a road friction coefficient according to vehicle running conditions even when a vehicle travels in the midst of low friction environments.

However, the aforesaid technique requires two road friction coefficients estimating means, one is an ordinal road friction coefficient estimating means and another is a low friction road dedicated friction coefficient estimating means. Accordingly, there is a defect that the control system becomes complicated, large-sized and expensive.

SUMMARY OF THE INVENTION

It is an object of the present invention to provide an inexpensive road friction coefficient estimating apparatus for a vehicle capable of efficiently estimating friction coefficients of road surfaces according to road conditions without complicating and up-sizing the apparatus.

To achieve the object, the road friction coefficient estimating apparatus for a vehicle, having an estimating means for estimating a road friction coefficient based on motion parameters indicative of a motion of said vehicle, comprises a road roughness detecting means for detecting a roughness of road surface and for producing a road roughness parameter indicating the roughness of road surface, wherein the estimating means is adapted to vary a responsibility of estimating the road friction coefficient according to the road roughness parameter.

DETAILED DESCRIPTION OF PREFERRED EMBODIMENTS

Figure 1:
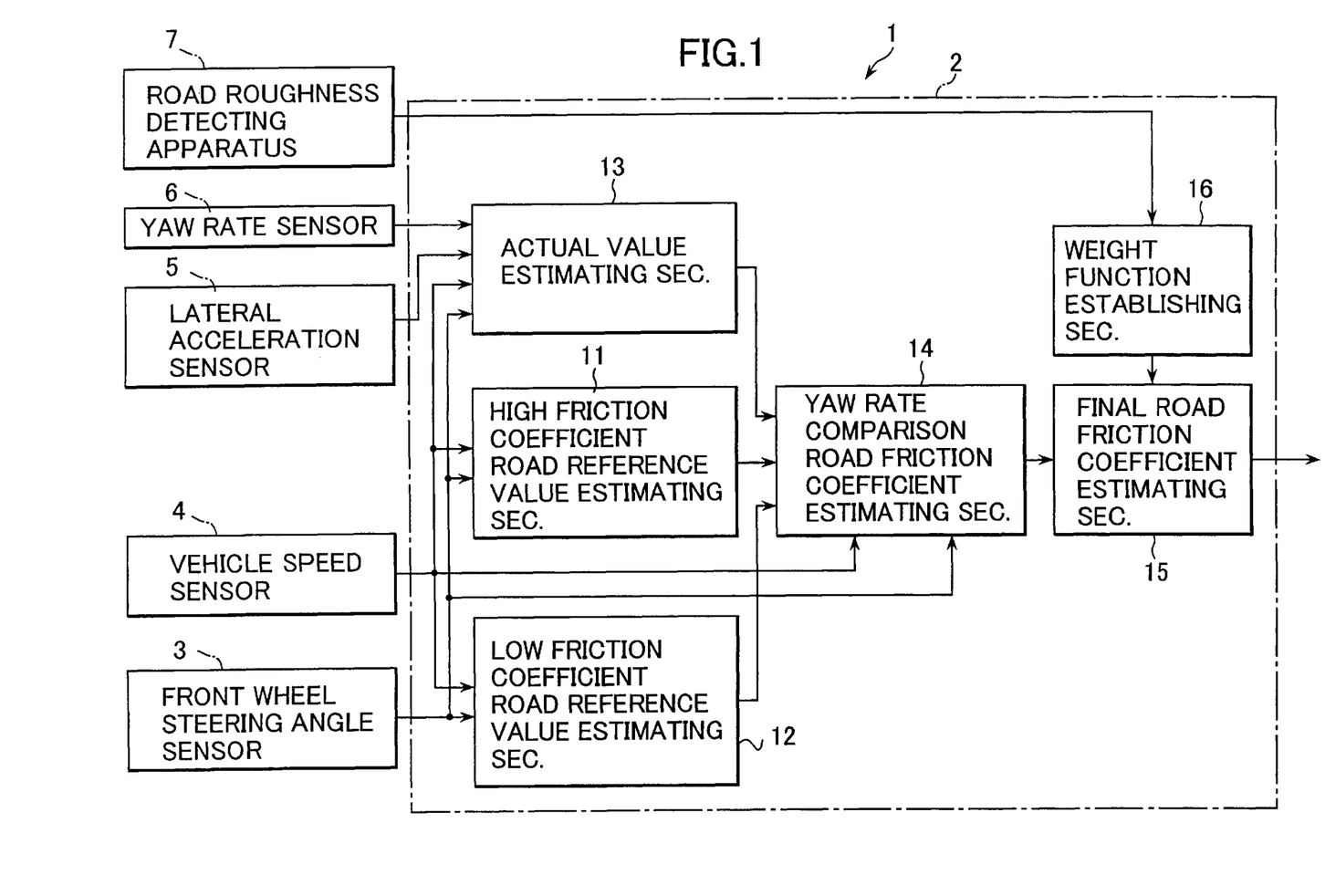
FIG. 1 is a functional block diagram showing a construction of a road friction coefficient estimating apparatus according to a first embodiment of the present invention.

Referring now to FIG. 1, reference numeral 1 denotes a road friction coefficient estimating apparatus and reference numeral 2 denotes a control section (road friction coefficient estimating means) of the road friction coefficient estimating apparatus 1. The control section 2 is connected with a front wheel steering angle sensor 3, a vehicle speed sensor 4, a lateral acceleration sensor 5 and a yaw rate sensor 6 so as to input a front wheel steering angle δfs, a vehicle speed Vs, a lateral acceleration $(dy^2/dt^2)$s, and a yaw rate (yaw angular velocity) $(d\phi/dt)$s respectively. A subscript "s" attached to respective parameters is for showing values detected by sensors.

Further, the control section 2 of the road friction coefficient estimating apparatus 1 is connected with a road roughness detecting apparatus 7 acting as a road roughness detecting means for inputting road roughness conditions. The road roughness detecting apparatus 7 is constituted by vibration sensors for detecting vertical, longitudinal and lateral vibrations of a vehicle or by a frontal image recognition apparatus. In employing the frontal image recognition apparatus, specifically, a pair of cameras laterally disposed on the ceiling of a passenger compartment take stereoscopic images of outside scenery. Then, distance information is obtained with respect to a pair of stereoscopic images by applying the principle of triangulation to the lateral deviation of the pair of stereoscopic images and distance images including three-dimensional distance distribution are produced. Further, the distance images are processed based on miscellaneous stored data and frontal road conditions or solid objects are recognized. Road roughness is judged from the number of edges in the image.

The control section 2 comprises a high friction coefficient road reference value estimating section 11, a low friction road reference value estimating section 12, an actual value estimating section 13, a yaw rate comparison road friction coefficient estimating section 14, a final road friction coefficient estimating section 15 and a weight function establishing section 16.

The high friction coefficient road reference value estimating section 11 inputs a vehicle speed Vs and a front wheel steering angle δfs, calculates a yaw rate, that is, a high friction coefficient road reference yaw rate $(d\phi/dt)H$ corresponding to the detected vehicle speed Vs and the detected front wheel steering angle δfs, based on a vehicle motion model obtained from an equation of motion of the vehicle on a road surface with high friction coefficient and outputs the yaw rate to the yaw rate comparison road friction coefficient estimating section 14.

Further, the high friction coefficient road reference value estimating section 11 outputs a high friction coefficient road reference yaw angular acceleration $(d^2\phi/dt^2)H$ and a lateral acceleration $(d^2y/dt^2)H$ in addition to the high friction coefficient road reference yaw rate $(d\phi/dt)H$ to the yaw rate comparison road friction coefficient estimating section 14. A subscript "H" attached to respective parameters is for showing parameters of the high friction coefficient road reference.

The low friction coefficient road reference value estimating section 12 inputs the vehicle speed Vs and the front wheel steering angle δfs, calculates a yaw rate, that is, a low friction coefficient road reference yaw rate $(d\phi/dt)L$ corresponding to the detected vehicle speed Vs and the detected front wheel steering angle δfs based on a vehicle motion model obtained from an equation of motion of the vehicle on a road surface with low friction coefficient and outputs the yaw rate to the yaw rate comparison road friction coefficient estimating section 14.

Further, the low friction coefficient road reference value estimating section 12 outputs a low friction coefficient road reference yaw angular acceleration $(d^2\phi(dt^2)L$ and a lateral acceleration $(d^2y/dt^2)L$ in addition to the low friction coefficient road reference yaw rate $(d\phi/dt)L$ to the yaw rate comparison road friction coefficient estimating section 14. A subscript "L" attached to respective parameters is for showing parameters of the low friction coefficient road reference.

Figure 2:
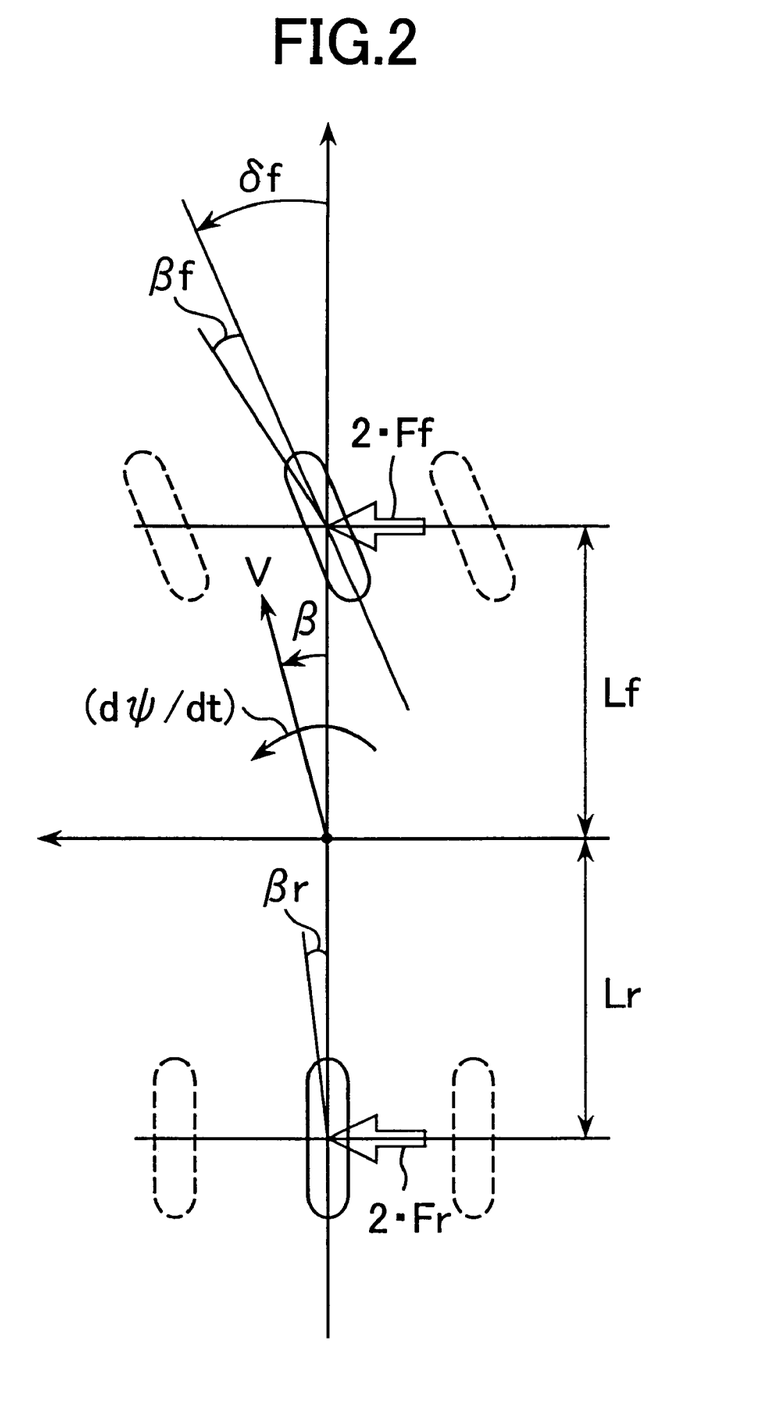
FIG. 2 is a diagram showing a two-wheel vehicle model equivalent to a four wheel vehicle.

The vehicle motion model used in the high friction coefficient road reference value estimating section 11 and the low friction coefficient road reference value estimating section 12 and the calculation of the respective parameters will be described by reference to FIG. 2. The equation of lateral transitional motion of a vehicle is:

$$M \cdot (d^2y/dt^2) = 2 \cdot F_f + 2 \cdot F_r \tag{1}$$

where M is mass of a vehicle; $F_f$, $F_r$ are cornering forces of front and rear wheels, respectively; and $(d^2y/dt^2)$ is lateral acceleration.

On the other hand, an equation of rotational motion around gravity center of the vehicle is expressed as:

$$I_z(d^2\phi/dt^2) = 2 \cdot F_f L_f - 2 \cdot F_r L_r \tag{2}$$

where $I_z$ is yaw moment of inertia of the vehicle; $L_f$, $L_r$ are distances from the center of gravity to the front and rear wheels, respectively; and $(d^2\phi/dt^2)$ is yaw angular acceleration.

The lateral acceleration $(d^2\phi/dt^2)$ is expressed as:

$$(d^2y/dt^2) = V \cdot ((d\beta/dt) + (d\phi/dt)) \tag{3}$$

where V is vehicle speed; β is slip angle of the vehicle; and (dβ/dt) is slip angular velocity of the vehicle.

The cornering forces have a response similar to a first-order time lag, however, in this case, this time lag is neglected. Further, letting the cornering forces be linearized introducing an idea of equivalent cornering power in which suspension characteristic is involved in tire characteristic, the cornering forces are expressed as follows:

$$F_f = -K_f \beta_f \tag{4}$$

$$F_r = -K_r \cdot \beta_r \tag{5}$$

where $K_f$, $K_r$ are equivalent cornering powers of front and rear wheels, respectively; and $\beta_f$, $\beta_f$ are lateral slip angles of front and rear wheels, respectively.

Using equivalent cornering powers taking the effect of roll and suspension of the vehicle into consideration, lateral slip angles $\beta_f$, $\beta_r$ are can be simplified as follows:

$$\beta_f = \beta + L_f (d\phi/dt)/V - \delta_f \tag{6}$$

$$\beta_r = \beta - L_r \cdot (d\phi/dt)/V \tag{7}$$

where $\delta_f$ is steering angle of front wheel.

Combining aforesaid equations of motion, following equations of state are obtained:

$$(dx(t)/dt) = A \cdot x(t) + B \cdot u(t) x(t) = [\beta (d\phi/dt)]^T u(t) = [\delta_f 0]^T \tag{8}$$

$$A = \begin{matrix} a_{11} & a_{12} \\ a_{21} & a_{22} \end{matrix}$$

$$B = \begin{matrix} b_{11} & b_{12} \\ b_{21} & b_{22} \end{matrix}$$

$$a_{11} = -2 \cdot (K_f + K_r)/(M \cdot V)$$

$$a_{12} = -1 - 2 \cdot (L_f K_f - L_r)/(M \cdot V^2)$$

$$a_{21} = -2 \cdot (L_{fK_f} - L_r \cdot K_r)/I_z$$

$$a_{22} = -2 \cdot (L_f^2 \cdot K_f + L_r^2 \cdot K_r)/(I_z \cdot V)$$

$$b_{11} = 2 \cdot K_f/(M \cdot V)$$

$$b_{21} = 2 \cdot L_f K_f/I_z$$

$$b_{12} = b_{22} = 0$$

In the high friction coefficient road reference value estimating section 11, a high friction coefficient road reference slip angular velocity (d β/dt)H and a high friction coefficient road reference yaw angular acceleration $(d^2\phi/dt^2)H$ are obtained by calculating $(dx(t)/dt) = [(d\beta/dt) (d^2\phi/dt^2)]^T$ in a vehicle operating condition (vehicle speed Vs, front wheel steering angle δfs) when equivalent cornering powers $K_f$, $K_r$ at 1.0 for example of road friction coefficient have been established beforehand in the formula (8). Then, a high friction coefficient road reference slip angle βH and a high friction coefficient road reference yaw rate $(d\phi/dt)H$ are obtained by integrating the slip angular velocity $(d\beta/dt)H$ and the yaw angular acceleration $(d^2\phi/dt^2)H$. Further, a high friction coefficient road reference front wheel slip angle $\beta_f H$ is calculated by substituting the high friction coefficient road reference slip angle $\beta H$ and yaw rate $(d\phi/dt)H$ into the aforesaid formula (6). Further, a high friction coefficient road reference lateral acceleration $(d^2y/dt^2)H$ is calculated by substituting the high friction coefficient road reference slip angular velocity $(d\beta/dt)H$ and yaw rate $(d\phi/dt)H$ into the aforesaid formula (3).

Similarly, in the low friction coefficient road reference value estimating section 12, a low friction coefficient road reference slip angular velocity $(d\beta/dt)L$ and a low friction coefficient road reference yaw angular acceleration $(d^2\phi/dt^2)L$ are obtained by calculating $(dx(t)/dt)=[(d\beta/dt)\ (d^2\phi/dt^2)]^T$ in a given vehicle operating condition (at vehicle speed Vs, front wheel steering angle $\delta fs$) when equivalent cornering powers $K_f$, $K_r$ at 0.3 for example of road friction coefficient have been established beforehand in the formula (8). Then, a low friction coefficient road reference slip angle $\beta L$ and a low friction coefficient road reference yaw rate $(d\phi/dt)L$ are obtained by integrating the calculated slip angular velocity $(d\beta/dt)L$ and yaw angular acceleration $(d^2\phi/dt^2)L$. Further, a low friction coefficient road reference front wheel slip angle $\beta_f L$ is calculated by substituting the low friction coefficient road reference slip angle $\beta L$ and yaw rate $(d\phi/dt)L$ into the aforesaid formula (6).

The actual value estimating section 13 is an observer formed by a vehicle motion model, to which a vehicle speed Vs, a front wheel steering angle $\delta fs$ and a yaw rate $(d\phi/dt)$ are inputted and an actual yaw rate $(d\phi/dt)0$ is estimated by calculation while actual vehicle behaviors are fed back. The actual yaw rate $(d\phi/dt)0$ estimated in the actual value estimating section 13 is outputted to the yaw rate comparison road friction coefficient estimating section 14.

Also, in addition to the yaw rate $(d\phi/dt)0$, a yaw angular acceleration $(d^2\phi/dt^2)0$ is outputted to the yaw rate comparison road friction coefficient estimating section 14. The subscript "0" attached to respective parameters outputted from the actual value estimating section 13 shows parameters outputted from the observer.

Figure 3:
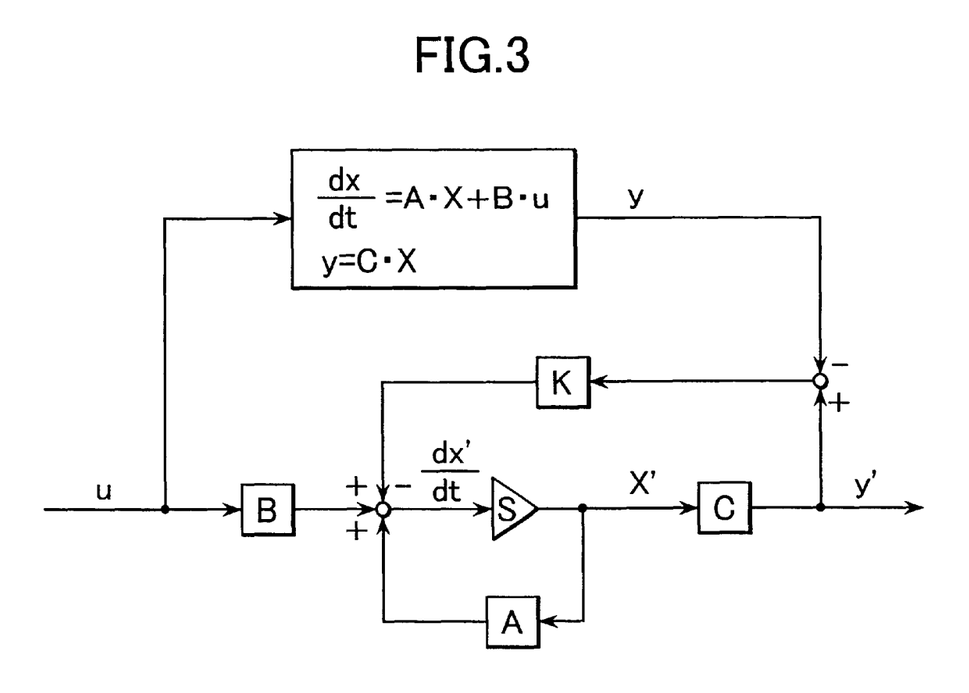
FIG. 3 is an explanatory diagram showing a construction of an observer.

Next, the construction of the observer according to this embodiment will be described by reference to FIG. 3. When a measureable output (output detectable by sensors) is shown as follows, $$y(t) = C \cdot x(t) \quad (9)$$

the construction of the observer is as follows:

$$(dx'(t)/dt) = (A - K \cdot C) \cdot x'(t) + K \cdot y(t) + B \cdot u(t) \quad (10)$$

where applying the observer to the vehicle motion model, $x(t)$ is state variable vector ($x'(t)$ means estimating value); $u(t)$ is input vector; A, B are coefficient matrixes of state of equations, respectively; $y(t)$ is observable sensor output vector which is expressed as $y(t)=[\beta s (d\phi/dt)s]^T$ ($\beta s$ is obtained by integrating a sensor vehicle slip angular velocity $(d\beta/dt)s$ which is obtained from sensor lateral acceleration $(d^2y/dt^2)s$ and sensor yaw rate $(d\phi/dt)s$ using the aforesaid formula (3)); C is matrix (unit matrix in this embodiment) showing the relationship between sensor outputs and state variables; K is feedback gain matrix which can be arbitrarily established.

$$C = \begin{matrix} 1 & 0 \\ 0 & 1 \end{matrix}$$

$$K = \begin{matrix} k_{11} & k_{12} \\ K_{21} & k_{22} \end{matrix}$$

If thus established feed-back gain matrix has a large value, the sensitivity of the system becomes high. As a result, the system is focused upon responsiveness rather than accuracy. On the other hand, if the feedback gain matrix has a small value, the sensitivity of the system becomes low. As a result, the system is focused upon accuracy and stability rather than responsiveness.

A yaw angular acceleration $(d^2\phi/dt^2)0$ and vehicle slip angular velocity $(d\beta/dt)0$ are calculated according to following formulas (11), (12) from the relationship described before:

$$(d^2\phi/dt^2)0 = a_{11} \cdot (d\phi/dt)0 + a_{12} \cdot \beta 0 + b_{11} \cdot \delta fs + k_{11} \cdot ((d\phi/dt)s - (d\phi/dt)0) + k_{12} \cdot (\beta s - \beta 0) \quad (11)$$

$$(d\beta/dt)0 = a_{21} \cdot (d\phi/dt)0 + a_{22} \cdot \beta 0 + k_{21} \cdot ((d\phi/dt)s - (d\phi/dt)0) + k_{22} \cdot (\beta s - \beta 0) \quad (12)$$

A yaw rate $(d\phi/dt)0$ and vehicle slip angle $\beta 0$ are obtained by integrating thus calculated yaw angular acceleration $(d^2\phi/dt^2)0$ and vehicle slip angular velocity $(d\beta/dt)0$, respectively. Further, a front wheel slip angle $\beta f0$ is calculated by substituting the vehicle slip angle $\beta 0$ and yaw rate $(d\phi/dt)0$ into the aforesaid formula (6).

During calculations in the high friction coefficient road reference value estimating section 11, the low friction coefficient road reference value estimating section 12 and the actual value estimating section 13, when the vehicle speed Vs is zero, the calculation can not executed due to the division by zero. Hence, when the vehicle travels at very low speeds, for example, below 10 km/h, the yaw rate and lateral acceleration is forced to be sensor values. That is:

$$(d\phi/dt)H = (d\phi/dt)L = (d\phi/dt)0 = (d\phi/dt)s$$

$$(d^2y/dt^2)0 = (d^2y/dt^2)s$$

Further, the vehicle slip angle can be derived from the geometric relationship of the turning on the stationary circle as follows:

$$\beta H = \beta L = \beta 0 = \delta f_s \cdot L_r / (L_f + L_r)$$

At this moment, since no cornering force is not generated, all of front wheel slip angles become zero:

$$\beta fH = \beta fL = \beta f0 = 0$$

The yaw rate comparison road friction coefficient estimating section 14 inputs the vehicle speed Vs, the front wheel steering angle $\delta fs$ of sensor value, the high friction coefficient road reference yaw rate $(d\phi/dt)H$, the high friction coefficient road reference yaw angular acceleration $(d^2\phi/dt^2)H$, the high friction coefficient road reference lateral acceleration $(d^2y/dt^2)H$, the low friction coefficient road reference yaw rate $(d\phi/dt)L$, the actually estimated yaw rate $(d\phi/dt)0$ and the actually estimated yaw angular acceleration $(d^2\phi/dt^2)0$. Further, if a calculation condition which will be described hereinafter is satisfied, a new road friction coefficient $\mu\lambda n$ is calculated from the high friction coefficient road reference yaw rate $(d\phi/dt)H$, the low friction coefficient road reference yaw rate $(d\phi/dt)L$ and the actually estimated yaw rate $(d\phi/dt)0$ in accordance with the following formula (13) and this new road friction coefficient $\mu\lambda n$ is outputted to the final road friction coefficient estimating section 15.

The road friction coefficient $\mu\gamma n$ is calculated according to the following formula (13):

Road friction coefficient $$\mu\gamma n=((\mu H-\mu L)\cdot(d\phi/dt)0+\mu L\cdot(d\phi/dt)H-\mu H\cdot(d\phi/dt)L/((d\phi/dt)H-(d\phi/dt)L) \quad (13)$$

where $\mu H$ is road friction coefficient estimated in the high friction coefficient road reference value estimating section 11 (for example 1.0); and $\mu L$ is road friction coefficient estimated in the low friction coefficient road reference value estimating section 12 (for example 0.3).

That is, a linear function is formed using parameters high friction coefficient road reference yaw rate $(d\phi/dt)H$ and low friction coefficient road reference yaw rate $(d\phi/dt)L$ and the road friction coefficient $\mu\gamma n$ is obtained by substituting a yaw rate $(d\phi/dt)0$ into this linear function. It should be noted that the value of the road friction coefficient $\mu\gamma n$ is restricted between a specified upper limit (for example 1.0) and a specified lower limit (for example 0.3).

Further, in the yaw rate comparison road friction coefficient estimating section, following conditions have been established beforehand:

[Condition 1—1]

No calculation is performed when the vehicle travels at low speeds (for example, the vehicle speed Vs is below 10 km/h) or when the vehicle has a large steering angle (for example, when the steering angle exceeds 500 degrees). In describing the motion of a vehicle, although the actual motion of the vehicle has multiple degrees of freedom, in this embodiment the vehicle motion is expressed by only two degrees of freedom, lateral motion and rotational motion around a vertical axis in order to simplify calculation. Further, the two wheel model is used to describe the motion of the vehicle. Accordingly, when the vehicle speed is low or the steering angle is large, there is a large difference of behavior between the model and the actual vehicle.

[Condition 1–2]

No calculation is performed in case where the absolute value of yaw rate is small. When the yaw rate is small, the effects of noises or disturbances become relatively large. For example, when the absolute value of the yaw rate $(d\phi/dt)0$ is below 1.5 degrees/second, the calculation is not performed.

[Condition 1–3]

No calculation is performed in case where cornering forces are small, that is, the absolute value of lateral acceleration proportional to the cornering forces is small. When the cornering forces are small, the effect of noises or disturbances become relatively large with respect to the effect of road friction coefficients. For example, in case where the absolute vale of the high friction coefficient road reference lateral acceleration $(d^2y/dt^2)H$ is smaller than 0.15 G, the calculation is not performed.

[Condition 1–4]

Sometimes, the yaw rate response to the steering angle input is delayed in time by road friction coefficients. If the calculation of road friction coefficient is performed while this delay occurs, the calculation is accompanied by large errors. Accordingly, no calculation is performed when the time delay is large or it is judged that errors by delay will become large. For example, if it is judged that the time delay excepting a leading edge of yaw rate enlarges errors, the calculation is not performed. The leading edge of yaw rate is judged from (yaw rate)·(yaw angular acceleration).

[Condition 1–5]

No calculation is performed in case where the absolute value of he difference between a high friction coefficient road reference yaw rate and a low friction coefficient road reference yaw rate does not have an adequate size with respect to the effect of noises and disturbances. For example, in case where the absolute value of the difference between a high friction coefficient road reference yaw rate $(d\phi/dt)H$ and a low friction coefficient road reference yaw rate $(d\phi/dt)L$ does not reach 1 degree/second, the calculation is not performed.

In the first embodiment of the present invention, the high friction coefficient road reference value estimating section 11, the low friction coefficient road reference value estimating section 12, the actual value estimating section 13 and the yaw rate comparison road friction coefficient estimating section 14 form a first road friction coefficient estimating means.

The final road friction coefficient estimating section 15 inputs a new road friction coefficient $\mu\gamma n$ from the yaw rate comparison road friction coefficient estimating section 14 and inputs a weigh function $\kappa_1$ which will be described hereinafter from the weight function establishing section 16. Further, a final present road friction coefficient $\mu\gamma$ is calculated by weight-averaging a final road friction coefficient $\mu_{n-1}$ previously estimated and a road friction coefficient $\mu\gamma n$ from the yaw rate comparison road friction coefficient estimating section 14 according to the following formula (14). Thus calculated road friction coefficient $\mu\gamma$ is outputted from the control section 2 of the road friction coefficient estimating apparatus 1. In the first embodiment of the present invention, this final road friction coefficient estimating section 15 forms a second road friction coefficient estimating means $$\mu\gamma=\mu_{n-1}+\kappa_1\cdot(\mu\gamma n-\mu_{n-1}) \quad (14)$$

The weight function establishing section 16 inputs a state of roughness of road surface from the road roughness detecting means 7 and establishes the weight function $\kappa_1$ according to the state of roughness of a road surface and outputs the $\kappa_1$ to the final road friction coefficient estimating section 15. The state of roughness of road surface is expressed as a number of concave and convex parts of a road surface per a specified distance. In order to raise the follow-up characteristic with respect to changes of road friction coefficients, the more the number of concave and convex parts larger than a specified level per a specified distance, the closer the weight function $\kappa_1$ to 1 so as to increase the influence of a term $(\mu\gamma n-\mu_{n-1})$ of the formula (14) in order to enhance responsibility to the change of road friction coefficients and on the other hand, the less the number of concave and convex parts, the closer the weight function $\kappa_1$ to 0 so as to reduce the influence of a term $(\mu\gamma n-\mu_{-1})$ of the formula (14) in order to raise accuracy and stability with respect to the change of road friction coefficients.

That is, this is because when the vehicle travels on ordinary good roads, the road friction coefficient continues to be a high friction coefficient value almost constantly and also the roughness of road surface is kept to be small. Hence, by establishing the weigh function $K_1$ to a value close to 0, as described above, it can be avoided that the road friction coefficient $\mu\gamma$ is established erroneously at a low friction coefficient value due to temporary disturbances and sensor noises.

On the other hand, in winter season, when the vehicle enters into a mountain cove or a tunnel, the state of roughness of such road surfaces is relatively large. Particularly, on snowy roads, the road friction coefficient $\mu\gamma$ is outputted to a low value swiftly by establishing the weight function $\kappa_1$ to a value close to land showing a state of roughness of road surface peculiar to roads with low friction coefficient.

According to the first embodiment, since the weight function $\kappa_1$ of the final road friction coefficient estimating section 15 is made variable, the estimation of road friction coefficient can be performed with a single road friction coefficient estimating means while the estimation being accompanied by both responsibility and accuracy. Further, the road friction coefficient estimating apparatus 1 is not made more complicated and more up-sized by this invention. Accordingly, the manufacturing cost can be kept low.

Thus, according to the first embodiment, the weight function establishing section 16 is designed such that as the state of road roughness is large, the weight function $\kappa_1$ is closer to 1, and contrarily as the state of road roughness is small, the weight function $\kappa_1$ is closer to 0, however, the weight function $\kappa_1$ may be designed so as to change over from 0.3 to 0.8 for example, when the state of road roughness exceeds a specified threshold value. Further, in the first embodiment, a new road friction coefficient $\mu \gamma$n is designed so as to be obtained by comparing the actual value of yaw rate with the high friction coefficient road reference value and the low friction coefficient road reference value, however this road friction coefficient $\mu \gamma$ may be obtained by comparing parameters other than yaw rate, for example, lateral acceleration or vehicle slip angle with the high and low friction coefficient road reference values. Further, in this embodiment, the road friction coefficient $\mu \gamma$n is designed so as to be obtained by comparing the actual value calculated by the observer with the high and low friction coefficient road reference values, however the new road friction coefficient may be estimated by an adaptive control and the like.

Figure 4:
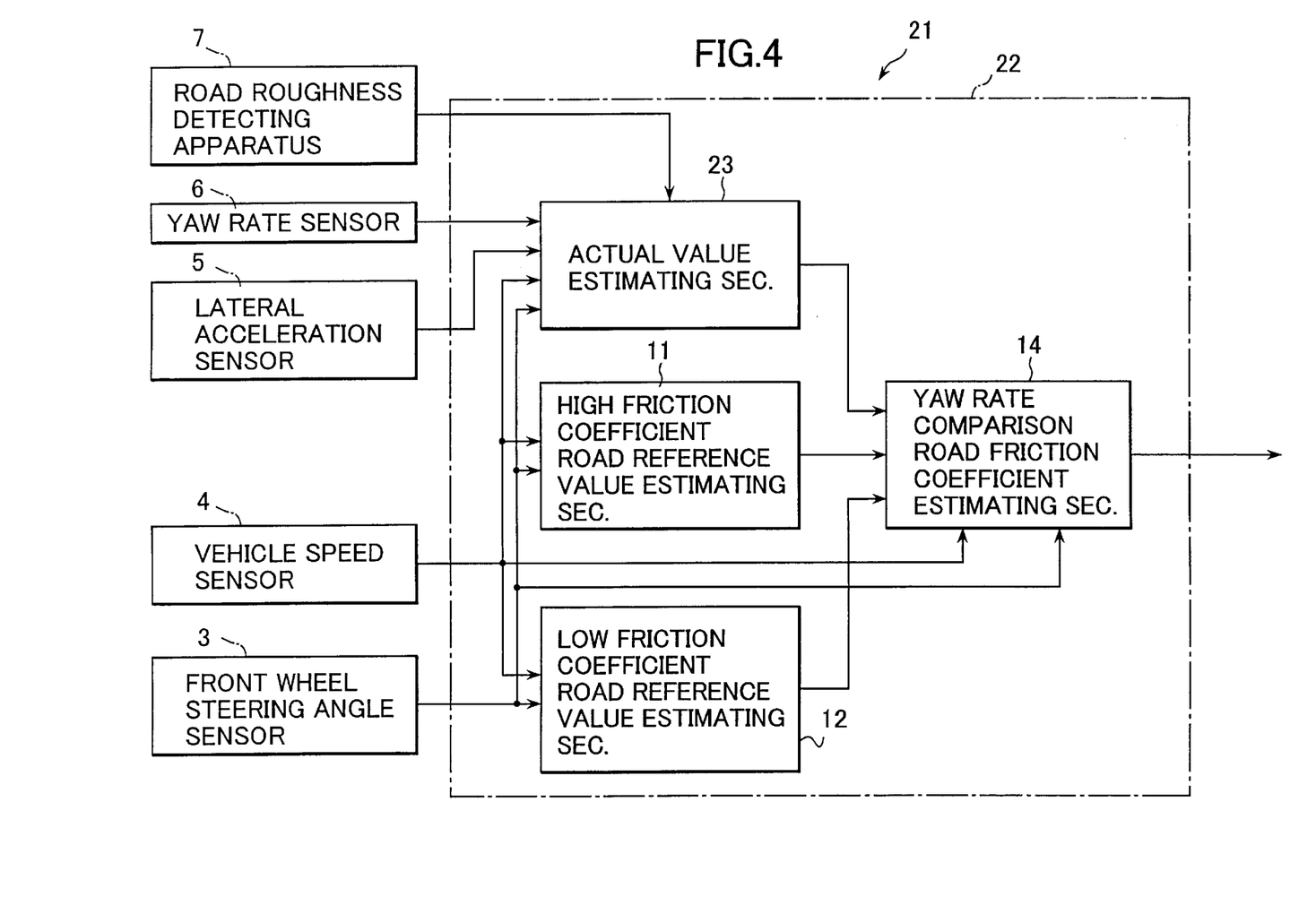
FIG. 4 is a functional block diagram showing a construction of a road friction coefficient estimating apparatus according to a second embodiment of the present invention.

FIG. 4 is a functional block diagram showing a road friction coefficient estimating apparatus according to a second embodiment. The major difference of this second embodiment from the first embodiment is that the feedback gain matrix K of the observer in the actual value estimating section 13 of the first embodiment is variable according to the state of road roughness so as to make the responsibility of road friction coefficient Estimation variable. The functional blocks which are identical in both embodiments are denoted by identical reference numbers and further descriptions will be omitted.

That is, a control section 22 (road friction coefficient estimating means) of a road friction coefficient estimating apparatus 21 according to the second embodiment comprises the high friction coefficient road reference value estimating section 11, the low friction coefficient road reference value estimating section 12, an actual value section 23 and the yaw rate comparison road friction coefficient estimating section 14.

The actual value estimating section 23 is an observer formed by a vehicle motion model, to which a vehicle speed Vs, a front wheel steering angle $\delta$fs and a yaw rate (d$\phi$/dt) are inputted and an actual yaw rate (d$\phi$/dt)0 is estimated by calculation while actual vehicle behaviors are fed back.

Also, the actual value estimating section 23 inputs A state of road roughness from the road roughness detecting apparatus 7 and according to this state of road roughness a feed-back gain matrix K in the formula (10) can be varied. That is, respective elements of the matrix, $k_{11}$, $k_{12}$, $k_{21}$, $k_{22}$ are variable.

As described before, the system becomes sensitive if this feedback gain matrix K is established to be large and as a result the system is focused upon responsibility rather than accuracy. On the other hand, if the feedback gain matrix has a small value, the sensitivity of the system becomes low. As a result, the system is focused upon accuracy and stability rather than responsiveness. Accordingly, specifically, the respective elements of the feed-back gain matrix, $k_{11}$, $k_{12}$, $K_{21}$, $k_{22}$ are established to a large value so as to increase the feed-back of the state quantity and to more reflect the actual value upon the state quantity estimation value. The respective elements of the matrix, $k_{11}$, $k_{12}$, $K_{21}$, $k_{22}$ may be changed over to different values in case where the state of road roughness exceeds a predetermined threshold value.

According to the second embodiment, similarly to the first embodiment, road friction coefficients can be estimated with a single road friction coefficient estimating means while being accompanied by both responsibility and accuracy. Also, road friction coefficients can be estimated without making the apparatus more complicated and more up-sized at low cost.

An actual yaw rate (d$\phi$/dt)0 estimated in the actual value estimating section 23 is outputted to the yaw rate comparison road friction coefficient estimating section 14. Also, a yaw angular acceleration $(d_2\phi/dt_2)$0 is outputted to the yaw rate comparison road friction coefficient estimating section 14.

According to the second embodiment, the new road friction coefficient $\mu \lambda$n calculated in the yaw rate comparison road friction coefficient estimating section 14 may be outputted as a final road friction coefficient directly or may be outputted as a final friction coefficient after being weight-averaged as described in the final road friction coefficient estimating section 15 of the first embodiment. Further, in the second embodiment, the new road friction coefficient $\mu \gamma$n is obtained by comparing the actual yaw rate (d$\phi$/dt)0 with the high friction coefficient road reference value and the low friction coefficient road friction coefficient road reference value, however, parameters other than yaw rate, for example, lateral acceleration or vehicle slip angle, may be used in place of yaw rate.

While the presently preferred embodiments of the present invention have been shown and described , it is to be understood that these disclosures are for the purpose of illustration and that various changes and modifications may be made without departing from the scope of the invention as set forth in the appended claims.

What is claimed is:

1. A road friction coefficient estimating apparatus for a vehicle, comprising:

estimating means for estimating a road friction coefficient based on motion parameters indicative of a motion of said vehicle, and road roughness detecting means for detecting roughness of a road surface and for producing a road roughness parameter indicating said roughness of the road surface;

wherein said estimating means is adapted to vary follow-up characteristic for a change of said road friction coefficient by changing responsiveness for estimating said road friction coefficient according to said roughness parameter, wherein said estimating means is adapted to raise said follow-up characteristic by enhancing responsiveness for estimating said road friction coefficient when the number of concave and convex parts as indicating a state of said roughness is larger than a specified level per a specified distance.

2. A road friction coefficient estimating apparatus for a vehicle, comprising:

estimating means for estimating a road friction coefficient based on motion parameters indicative of a motion of said vehicle, and road roughness detecting means for detecting roughness of the road surface and for producing a road roughness parameter indicating said roughness of road surface;

wherein said estimating means is adapted to vary follow-up characteristic for a change of said road friction coefficient by changing responsiveness for estimating said road friction coefficient according to said roughness parameter, said estimating means comprises:

first road friction coefficient estimating means for calculating a first road-friction coefficient based on said motion parameters of said vehicle;

weight function establishing means for setting a weight function according to said road roughness parameter; and second road friction coefficient estimating means for calculating a weighted average between said first road friction coefficient and said second road friction coefficient previously estimated according to said weight function as a weight multiplier and for outputting said second road friction coefficient.

3. The apparatus according to claim 2, wherein said weight function varies according to said road roughness parameter to raise said follow-up characteristic by enhancing said responsiveness for estimating said road friction coefficient when the number of concave and convex parts as indicating a state of said roughness of road surface is larger.

4. The apparatus according to claim 2, wherein said weight function varies according to said road roughness parameter to raise accuracy and stability with respect to the change of said road friction coefficient by reducing said responsiveness for estimating said road friction coefficient when the number of concave and convex parts as indicating the state of said roughness is less than a specified level per a specified distance.

5. A road friction coefficient estimating apparatus for a vehicle, comprising:

estimating means for estimating a road friction coefficient based on motion parameters indicative of a motion of said vehicle, and road roughness detecting means for detecting a roughness of road surface and for producing a road roughness parameter indicating said roughness of road surface;

wherein said estimating means is adapted to vary follow-up characteristic for a change of said road friction coefficient by changing responsiveness for estimating said road friction coefficient according to said roughness parameter, wherein said estimating means includes an actual value estimating section in which an actual value of motion parameter is calculated, a high friction coefficient road reference value estimating section in which a high friction coefficient road reference value is calculated based on a high friction coefficient road vehicle motion model, a low friction coefficient road reference value estimating section in which a low friction coefficient road reference value is calculated based on a low friction coefficient road vehicle motion model, and a road friction coefficient estimating section in which said road friction coefficient is calculated based on said high friction coefficient road reference value, said low friction coefficient road reference value and said actual value of said motion parameter, wherein said actual value estimating section includes an observer having a feedback gain matrix to be varied according to said road roughness parameter.

6. The apparatus according to claim 5, wherein:

said motion parameter is adapted to be a yaw rate.

7. The apparatus according to Claim 5, wherein:

said feedback gain matrix is established to be large when said road roughness parameter is large so as to raise follow-up characteristic by enhancing said responsiveness for estimating said road friction coefficient.

8. The apparatus according to claim 5, wherein:

said feedback gain matrix is established to be small when said road roughness parameter is small so as to raise accuracy and stability with respect to the change of said road friction coefficient by reducing said responsiveness to the change of said road friction coefficient.

9. A road friction coefficient estimating apparatus for a vehicle, comprising:

estimating means for estimating a road friction coefficient based on motion parameters indicative of a motion of said vehicle, and road roughness detecting means for detecting a roughness of road surface and for producing a road roughness parameter indicating said roughness of road surface;

wherein said estimating means is adapted to vary follow-up characteristic for a change of said road friction coefficient by changing responsiveness for estimating said road friction coefficient according to said roughness parameter;

wherein said estimating means is adapted to raise accuracy and stability with respect to the change of said road friction coefficient by reducing said responsiveness for estimating said road friction coefficient when the number of concave and convex parts as indicating the state of said roughness is less than a specified level per a specified distance.

* * * * *